US005750409A

United States Patent [19]

Herrmann et al.

[11] Patent Number: 5,750,409
[45] Date of Patent: May 12, 1998

[54] PENTACYCLIC COMPOUNDS AND THEIR USE AS ABSORPTION OR FLUORESCENT DYES

[75] Inventors: Rupert Herrmann; Hans-Peter Josel, both of Weilheim; Karl-Heinz Drexhage; Jutta Arden-Jacob, both of Siegen, all of Germany

[73] Assignee: Boehringer Mannheim GmbH, Mannheim, Germany

[21] Appl. No.: 454,440

[22] Filed: May 30, 1995

Related U.S. Application Data

[63] Continuation-in-part of Ser. No. 94,015, Sep. 7, 1993, abandoned.

[30] Foreign Application Priority Data

Nov. 18, 1991 [DE] Germany ............ 41 37 934.9

[51] Int. Cl.⁶ ............ G01N 33/557; G01N 33/536; C07D 221/18; C07D 491/00
[52] U.S. Cl. ............ 436/517; 436/536; 436/172; 436/800; 435/7.1; 546/42; 546/48
[58] Field of Search ............ 436/512, 513, 436/517, 536, 164, 166, 172, 800, 815; 435/7.1; 546/36, 48, 42

[56] References Cited

U.S. PATENT DOCUMENTS

| | | | |
|---|---|---|---|
| 4,622,400 | 11/1986 | Hammond | 546/179 |
| 4,900,686 | 2/1990 | Arnost et al. | 436/546 |
| 5,256,799 | 10/1993 | Field et al. | 548/469 |

*Primary Examiner*—Ponnathapura Achutamurthy
*Attorney, Agent, or Firm*—Felfe & Lynch

[57] ABSTRACT

Pentacyclic derivatives having the general formulae (Ia), (Ib) and (Ic)

denote: hydrogen, alkyl with 1 to 20 carbon atoms polyoxyhydrocarbyl, phenyl, phenylalkyl with 1 to 3 carbon atoms in the alkyl chain, wherein the alkyl residues or/and phenyl residues can be substituted by one or several hydroxy, halogen, sulfo, carboxy or alkoxycarbonyl groups in which alkoxy can have 1 to 4 carbon atoms;

$R^7$ denotes an alkyl group with 1 to 7 carbon atoms, substituted by at least one halogen, or denotes a carboxyalkyl group or a phenyl group which is substituted by a carboxy or alkoxycarbonyl group located at the o-position relative to the carbon atom bound to the pentacyclic ring system and by at least one halogen, wherein alkoxy can have 1 to 4 carbon atoms, or a carboxymethylene-oxy-alkyloxy group; the residues $R^{14}$ and $R^{15}$ as well as the positions on the rings in the formulae that are not marked by specific symbols denote any desired substituents which may optionally be linked together;

the two bonds marked by a broken line mean that the two carbon atoms which are joined by the bond marked by a broken line can be linked together by a single or double bond;

and $X^-$ is a counterion; as well as their derivatives activated at least at one of the residues $R^1$, $R^7$ or/and $R^{13}$.

The compounds can be used as absorption or fluorescent dyes, in particular as markers for hapten/antibody/protein conjugates, as laser dyes and as an absorption medium for solar collectors.

20 Claims, No Drawings

PENTACYCLIC COMPOUNDS AND THEIR USE AS ABSORPTION OR FLUORESCENT DYES

This is a continuation in part of application Ser. No. 094,015, filed Sep. 7, 1993, now abandoned.

BACKGROUND OF THE INVENTION

The present invention concerns new pentacyclic compounds with a structure similar to rhodamine as well as their use as absorption dyes and in particular as fluorescent dyes.

Numerous rhodamine derivatives are known which as hydrophilic derivatives with appropriate reactive groups can be used as markers (label substance). After reacting e.g. N-hydroxysuccinimide esters of tetramethyl-carboxyrhodamine or carboxyrhodamine 101 (RHODOS) with proteins or haptens containing amino groups one obtains compounds that are labelled which can be used in diagnostic systems.

Examples of such hapten-fluorescent conjugates (HFC) are described in EP-A-285179; however, the compounds described have absorption maxima at wavelengths of <600 nm.

Only a few rhodamines are known with absorption maxima of >600 nm, e.g. rhodamine 700/800. The production of conjugates of these compounds has not been described previously.

As a rule, it is expedient to be able to use cheap light sources for diagnostic systems such as e.g. laser diodes (670/760 nm) or cheap lasers (He/Ne:633 nm); however, these light sources cannot be used for the previously known rhodamine compounds with an absorption maximum of <600 nm that are used for example for hapten-fluorescent conjugates.

Depending on the analyte concentration combinations of fluorescent latices with hapten-fluorescent conjugates are also used for diagnostic applications. Such combinations have also not been previously described for the aforementioned favourable wavelength regions in which cheap light sources can be used.

SUMMARY OF THE INVENTION

The object of the present invention is to provide new pentacyclic compounds with a rhodamine-like structure whose absorption maxima are in a wavelength region of >600 nm, preferably >630 nm and which can be used to produce hapten-fluorescent conjugates or/and fluorescent latices for which it is possible to also use cheap light sources such as the aforementioned laser diodes or cheap lasers. This object is achieved by the present invention.

The invention concerns pentacyclic derivatives having the general formula Ia, Ib and Ic

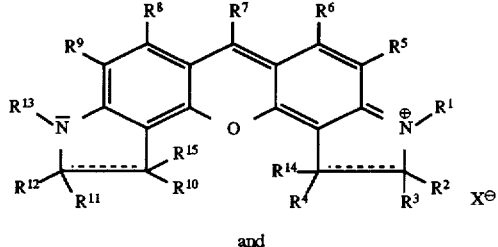

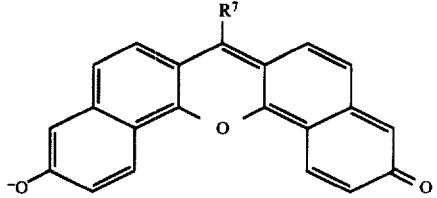

in which $R^1$ and $R^{13}$ are the same or different and denote: hydrogen, alkyl with 1 to 20, preferably 1 to 7 carbon atoms, polyoxyhydrocarbyl units, phenyl, phenylalkyl with 1 to 3 carbon atoms in the alkyl chain, wherein the alkyl residues or/and phenyl residues can be substituted by one or several hydroxy, halogen, sulfo, carboxy or alkoxycarbonyl groups in which alkoxy can have 1 to 4 carbon atoms;

$R^7$ denotes an alkyl group with 1 to 20, preferably 1 to 7 carbon atoms substituted by at least one halogen, or denotes a phenyl group which is substituted by a carboxy or alkoxycarbonyl group located at the opposition relative to the carbon atom bound to the pentacyclic ring system and by at least one halogen, wherein alkoxy can have 1 to 4 carbon atoms, or a carboxyalkyl group or a carboxymethylene-oxy-alkyloxy group; the two bonds of the general formula (Ia) and (IIa) marked by a broken line mean that the two carbon atoms which it joins can be linked together by a single or double bond whereby double bonds are preferred, and $X^-$ is a counterion; the residues $R^{14}$ and $R^{15}$ are the same or different and denote any desired substituents; as well as their derivatives activated at least at one of the residues $R^1$, $R^7$ or/and $R^{13}$.

Preferred embodiments of the compounds of formula (Ia) and (Ib) according to the present invention are compounds wherein $R^1$ and/or $R^{13}$ denote hydrogen, alkyl with 1 to 4 carbon atoms which optionally is substituted by a hydroxy, halogen, carboxy, alkoxycarbonyl or sulfo group, or benzyl.; $R^1$ and/or $R^{13}$ are polyoxyhydrocarbyl units such as polyethers, polyols, soluble carbohydrates and derivatives thereof or water-soluble polymers; $R^7$ is a perhalogenated, especially perfluorinated, alkyl group with 1 to 3 carbon atoms; $R^7$ is a carboxyalkyl group with an alkyl chain length of 0 to 10 or a carboxylmethylene-oxy-alkyloxy group; $R^1$ and $R^{13}$ in compounds of formula Ia are not bridged with substituents at positions $R^{15}$ or $R^{14}$; one or both of the bonds of formula Ia and/or Ib marked by a broken line are double bonds; the counterion is a perchlorate or heptafluorobutyrate ion or a carboxy or sulfo ion formed from one of the residues; the activated derivative derived from one of the residues $R^1$, $R^7$ and/or $R^{13}$ is a N-hydroxy-succinimide ester and/or an acid chloride derived from the carboxyl group.

The term "polyoxyhydrocarbyl units" within the meaning of the present invention is to be understood as polymeric or oligomeric organic residues which are linked together via ether bonds. This term is in particular understood as polyethers, polyols, soluble carbohydrates and derivatives thereof or water-soluble polymers. Polyoxyethylene groups

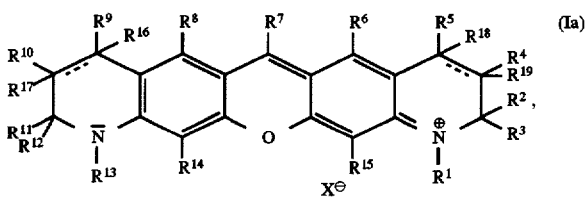

are particularly preferred whose size is such that the total compound is 800 to 1200, preferably about 1000. The aforementioned polyoxyethylene groups in the meaning of $R^1$ or/and $R^{13}$ improve the solubility, reduce unspecific binding of the compound to proteins and prevent dimerization.

The term "carboxyalkyl group" for $R^7$ is in particular understood as a carboxyalkyl group with an alkylene chain length of 0–10, whereby in this case $R^7$ denotes a carboxylic acid group when the alkyl chain length is 0. In the case of a carboxymethylene-oxy-alkyloxy group, alkyl preferably denotes 1 to 10 carbon atoms, particularly preferably 1 to 4 carbon atoms.

Compounds are also preferred which are characterized in that one or both of the broken line bonds of formulae Ia or/and Ib are double bonds.

This introduction of one or two double bonds at the positions of formula (Ia) marked by a broken line surprisingly leads to a pronounced shift to longer wavelengths.

Any desired substituents may be located at ring positions in the formulae designated $R^{14}$ and $R^{15}$ and at positions not marked with specific symbols and these may be optionally also linked together and are preferably hydrogen or, if desired, substituted alkyl with 1–20, in particular 1 to 7 carbon atoms.

Therefore R2, R3, R4, R5, R6, R8, R9, R10, R11, R12, R14, R15, R16, R17, R18, and R19, independently of each other, represent a hydrogen, an alkyl or a substituted alkyl having 1 to 20 carbons.

In compounds having formula (Ia) it is preferred that substituent R1 is not bonded with the substituent R15, and substituent R13 is not bonded with substituent R14.

When any of $R^2$, $R^3$, $R^4$, $R^5$, $R^6$, $R^8$, $R^9$, $R^{10}$, $R^{11}$, $R^{12}$, $R^{14}$, $R^{15}$, $R^{16}$, $R^{17}$, $R^{18}$, and $R^{19}$, are substituted alkyl, the substituents may be inert. In another embodiment at least two, and preferably two of the substituents $R^2$, $R^3$, $R^4$, $R^5$, $R^6$, $R^8$, $R^9$, $R^{10}$, $R^{11}$, $R^{12}$, $R^{14}$, $R^{15}$, $R^{16}$, $R^{17}$, $R^{18}$, or $R^{19}$, are linked together. Preferably the substituents are linked together forming pairs, for instance $R^1$ and $R^{15}$ and/or $R^{13}$ and $R^{14}$. This leads to a surprising increase in the quantum yield especially when $R^7$ is an alkyl residue substituted with halogen.

An alkyl group with 1 to 7 carbon atoms can be branch-chained or straight-chained; it preferably has 1 to 4 carbon atoms and is in particular e.g. methyl, ethyl, propyl, isopropyl, butyl, iso-butyl or tert.-butyl.

An alkoxy group in an alkoxycarbonyl group of $R^7$ preferably has 1 or 2 carbon atoms.

If an alkyl group represents the meaning of $R^7$ it in particular has 1 to 3 carbon atoms, and preferably has 1 or 2 carbon atoms for the other residues apart from $R^1$ and $R^{13}$.

A phenylalkyl group with 1 to 3 carbon atoms is in particular a phenethyl or benzyl group.

In the compounds according to the present invention having formula (Ia) and (Ib) at least one of the residues $R^1$, $R^7$ or/and $R^{13}$, and in particular residue $R^7$, is present in the form of an activated derivative. Such an activated derivative is derived in particular from a carboxylic acid or sulphonic acid group and is for example an acid ester, an acid halide, preferably bromide, and in particular chloride or a N-hydroxy-succinimide ester.

$R^1$ or/and $R^{13}$ are preferably e.g. hydrogen, alkyl with 1 to 4 carbon atoms which, if desired, is substituted by hydroxy, halogen, carboxy, alkoxycarbonyl or sulfo or they are polyoxyhydrocarbyl units, preferably polyethers, polyols, soluble carbohydrates and derivatives thereof (e.g. carbohydrates substituted by amino or acid groups), or water soluble polymers or benzyl. $R^7$ can preferably be a perhalogenated alkyl group with 1 to 3 carbon atoms or an o-carboxy or o-alkoxycarbonyltetrahalophenyl group in which alkoxy has the meaning; previously defined halogen in a perhalogenated alkyl or tetrahalogenated o-carboxy or o-alkoxycarbonyl-phenyl group denotes iodine, bromine, in particular chlorine and preferably fluorine. A perfluorinated alkyl group is e.g. trifluoromethyl or heptafluoropropyl. In a likewise preferred carboxyphenyl group within the meaning of $R^7$, the carboxy group is in the o-position relative to the carbon atom bound to the pentacyclic ring system. The introduction of at least one or several halogen atoms thereby surprisingly leads to a shift to longer wavelengths compared to known compounds not substituted with halogen (EP-A-0 285 179).

Any ion which is suitable for charge neutralisation and which is compatible with the cationic backbone may be used as a counterion; perchlorate is preferably used or the counterion may be derived from a carboxy or sulfo group of one of the residues. In addition to the selection and combination of residues, the choice of a suitable counterion allows the desired degree of lipophilicity to be optimized according to the intended application purpose. In addition to the incorporation of longer lipophilic residues, e.g. a heptafluoropropyl residue instead of a trifluoromethyl residue in the meaning of $R^7$ or/and longer and branched alkyl residues or/and aryl residues especially in the meaning of the residues $R^1$ and $R^{13}$, it is possible for example to further increase the lipophilicity by a specific anion exchange e.g. by replacing perchlorate by heptafluorobutyrate.

Examples of particularly preferred substituents in the meaning of $R^1$ and $R^{13}$ are: hydrogen, methyl, ethyl, 3-sulfopropyl, 4-sulfobutyl, 3-carboxypropyl, 4-carboxybutyl, 3-methoxycarbonylpropyl, 3-ethoxycarbonylpropyl, methoxy-ethoxy-ethyl, hydroxy-ethoxy-ethyl, benzyl. For use as hydrophilic markers it may be expedient to use asymmetrically substituted products in which the residues $R^1$ and $R^{13}$ are different and for example denote a 3-carboxypropyl or 4-carboxybutyl group ($R^1$) and a 3-sulfo-propyl or 4-sulfo-butyl group ($R^{13}$).

Preferred examples for residue $R^7$ are: trifluoromethyl, pentafluoroethyl, heptafluoropropyl, 3,4,5,6-halo-2-carboxyphenyl or 3,4,5,6-halo-2-ethoxycarbonylphenyl (halo=bromine, iodine and in particular chlorine or fluorine), or carboxyethyl.

Particularly preferred compounds according to the present invention having the formula (Ia), (Ib) or (Ic) are the compounds (1) to (24) set forth in the following; for which the absorption maxima ($\lambda_A$) the fluorescence maxima ($\lambda_F$) and the fluorescence quantum yields (Q) are stated. If not stated otherwise the details refer to slightly acidified ethanol as solvent at 20° C.

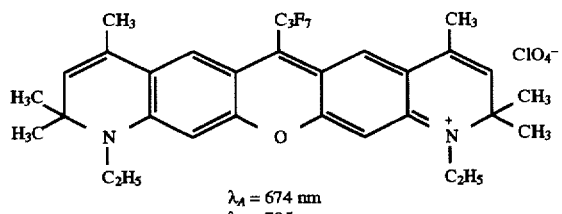

$\lambda_A = 674$ nm
$\lambda_F = 705$ nm
$Q_F = 57\%$

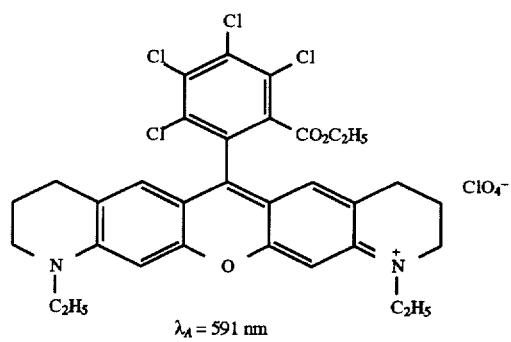
(2)
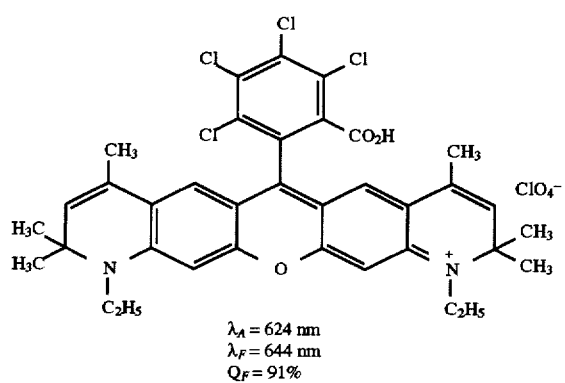
(3)
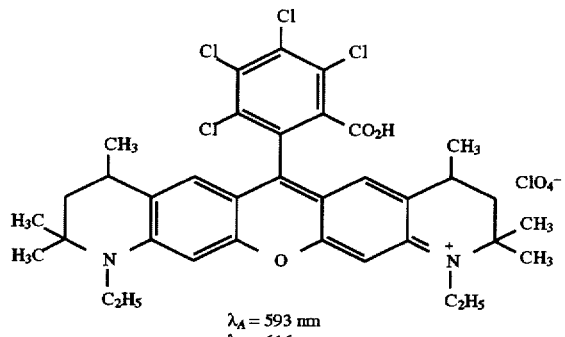
(4)
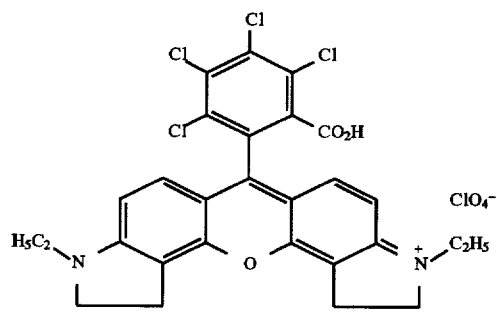
(5)
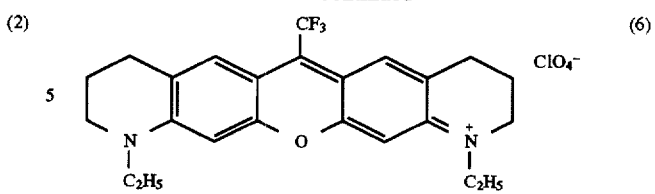
(6)
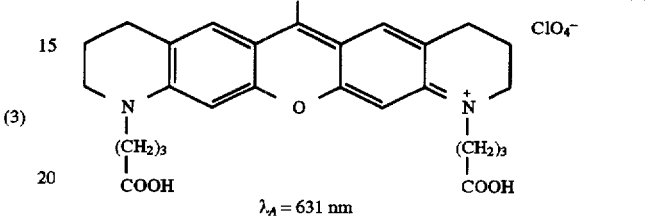
(7)
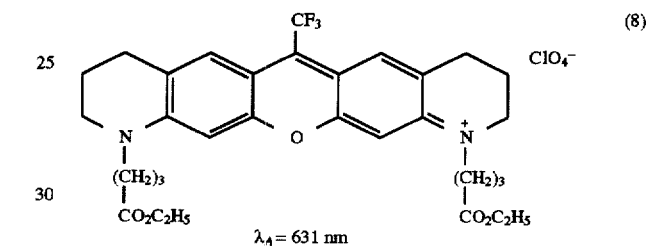
(8)
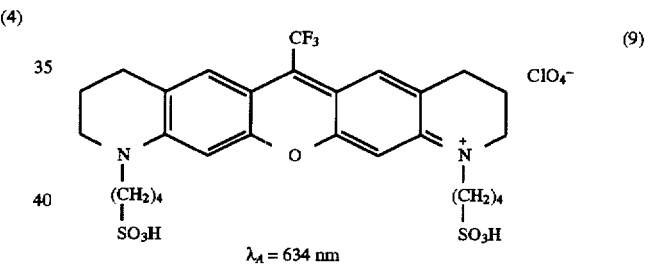
(9)
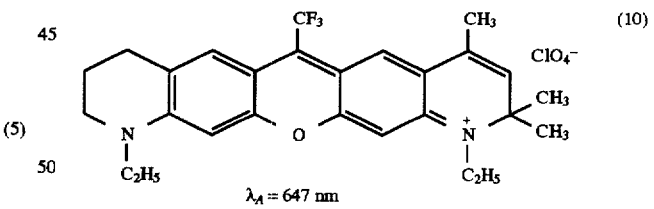
(10)
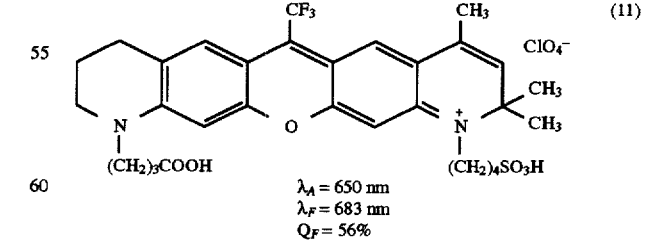
(11)

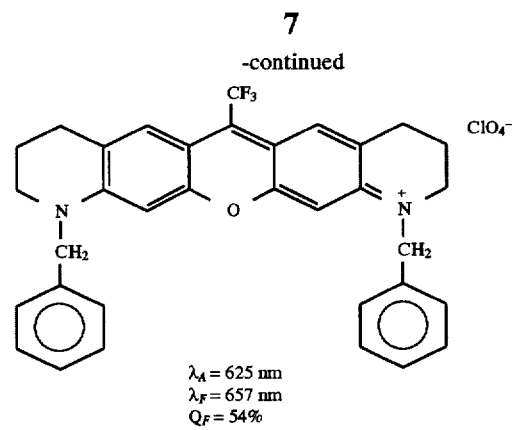
(12)
$\lambda_A = 625$ nm
$\lambda_F = 657$ nm
$Q_F = 54\%$
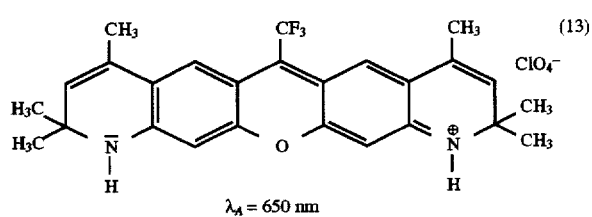
(13)
$\lambda_A = 650$ nm
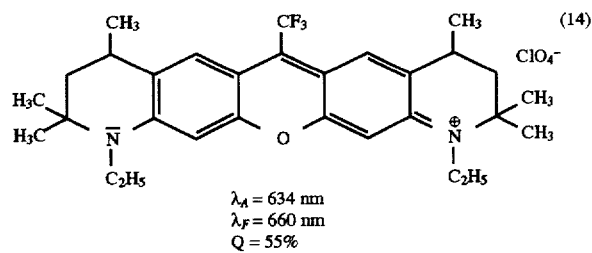
(14)
$\lambda_A = 634$ nm
$\lambda_F = 660$ nm
$Q = 55\%$
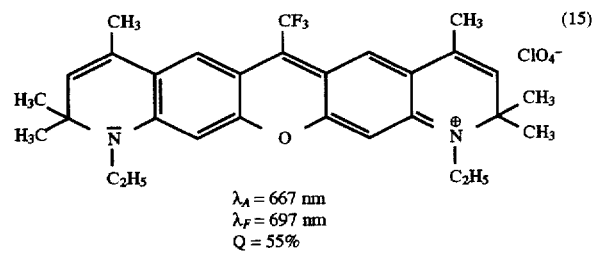
(15)
$\lambda_A = 667$ nm
$\lambda_F = 697$ nm
$Q = 55\%$
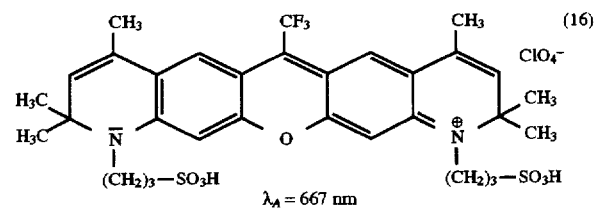
(16)
$\lambda_A = 667$ nm
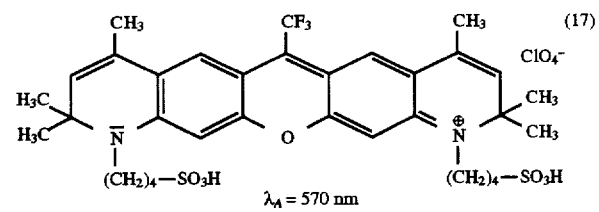
(17)
$\lambda_A = 570$ nm
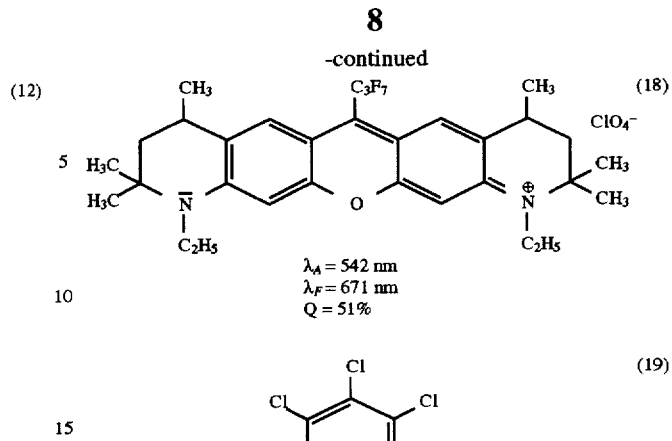
(18)
$\lambda_A = 542$ nm
$\lambda_F = 671$ nm
$Q = 51\%$
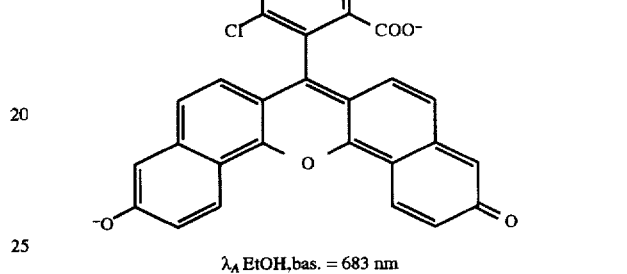
(19)
$\lambda_A$ EtOH,bas. = 683 nm
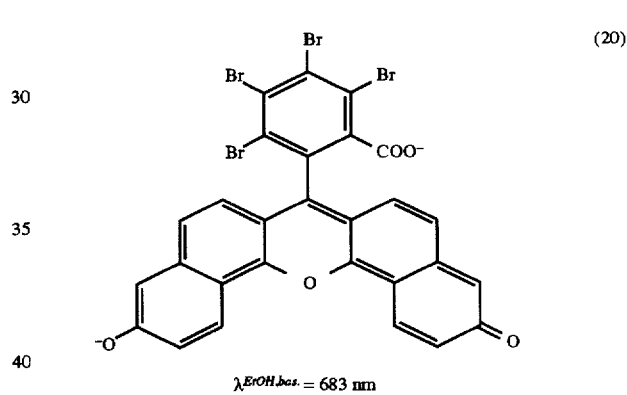
(20)
$\lambda^{EtOH,bas.} = 683$ nm
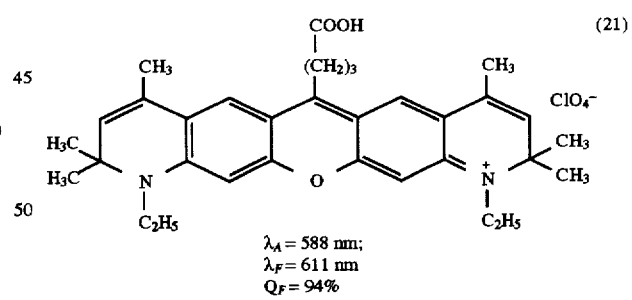
(21)
$\lambda_A = 588$ nm;
$\lambda_F = 611$ nm
$Q_F = 94\%$
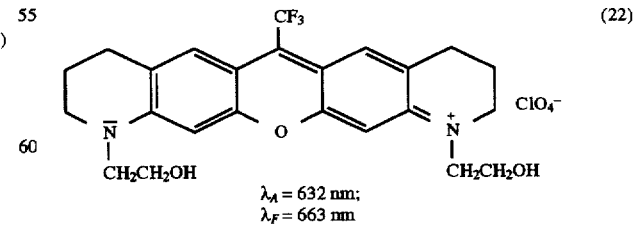
(22)
$\lambda_A = 632$ nm;
$\lambda_F = 663$ nm

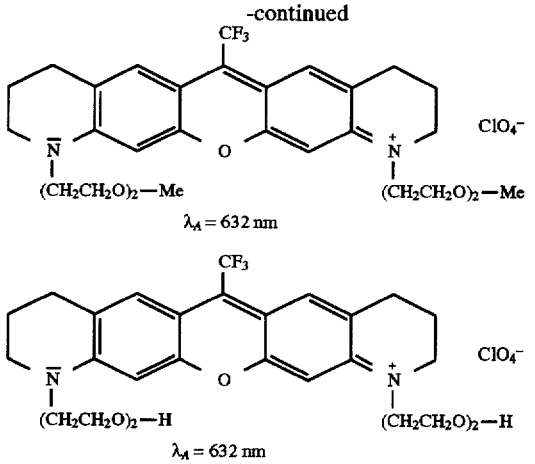

(23) $\lambda_A = 632$ nm

(24) $\lambda_A = 632$ nm

With regard to compounds (Ia) and (Ib) according to the present invention in which $R^7$ denotes halogenated o-carboxy or alkoxycarbonyl-phenyl, the new compounds according to the present invention can be produced in the usual manner for the synthesis of rhodamines by condensing 2 mol of an appropriate 3-aminophenol derivative (e.g. of N-ethyl-7-hydroxy-2,2,4-trimethyl-1,2,3,4-tetrahydroquinoline) with 1 Mol of an appropriate anhydride (e.g. phthalic acid anhydride derivative) (cf. e.g. "R ompps' Chemie Lexikon", 8th Edition, page 3580). The initial compounds are known or may be obtained in a known manner.

Compounds according to the present invention in which $R^7$ represents an alkyl group substituted by halogen such as e.g. $CF_3$ may be produced for example according to the process stated for rhodamine 700 (cf. N. F. Haley, J. Heterocyclic Chemistry, 14, 683 (1977).

Surprisingly, it is possible to synthesize the compounds according to the present invention in which $R^7$ denotes a halogenalkyl in good yields by reacting the corresponding aminophenyl-alkyl ether with the respective halogen acid anhydrides according to the following general reaction scheme:

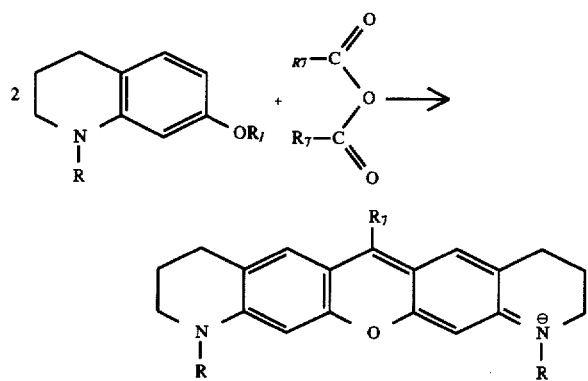

The appropriate aminophenyl-alkyl ether is incubated at room temperature under inert conditions, e.g. under a nitrogen atmosphere, with the halogen acid anhydride and subsequently retreated at a higher temperature (preferably ca. 100° C.) with concentrated acid (preferably with ca. 70% sulphuric acid).

The compounds of formula (Ic) may be obtained by reacting corresponding diphenols with the respective anhydrides. Rhodamine 700 known from the state of the art (cf. T. F. Johnston, R. H. Brady, W. Proffitt, Appl. Optics. 21(13), 2307 (1982)) has an absorption maximum of 643 nm at a quantum yield of ca. 20%; this compound differs from the compounds according to the present invention in that the residues $R^{13}$ and $R^{14}$ as well as $R^1$ and $R^{15}$ in formula (Ia) are bridged. Although in the case of the new compounds of formula (Ia) according to the present invention in which this cross-link is absent the wavelength is not shifted into a longer wavelength region, the quantum yield increases surprisingly to values between 50% (cf. e.g. compound 18) and 70% (cf. compound 6). The introduction of one or two double bonds leads to a shift into the long wavelength region; surprisingly the quantum yield is thereby not substantially diminished as would usually be expected as a result of enlarging the $\pi$ system.

The compounds according to the present invention thus provide new compounds which, due to their spectroscopic properties (absorption maxima in the range 600 nm and above and fluorescence between 600 and 700 nm; good quantum yield), are particularly suitable for absorption dyes and in particular fluorescent dyes which can be used in hapten/ and antibody/protein conjugates and for dyeing latices (fluorescent latices). As a result of their properties the compounds according to the present invention are suitable for use as laser dyes and are also very well suited as an absorption medium for solar collectors.

Substituent $R^7$ has substituents which attract electrons such as e.g. halogenated carboxyphenyl residues and perfluorinated alkyl residues which can surprisingly be used to obtain dyes with absorption wavelengths in the region of 600 nm or sometimes substantially more; the additional introduction of double bonds has the same effect and can further amplify it.

The halogenation of the carboxyphenyl residue $R^7$ leads for example to a shift of ca. 30 nm to longer wavelengths (from 558 nm to at least 591 nm) as well as to an increase in the quantum yield of ca. 10%; the introduction of one or two double bonds then leads to a further shift into the longer wavelength region.

The compounds according to the present invention can in addition be obtained in an activated form that is capable of coupling by appropriate derivatizations.

Thus according to the present invention it is possible by selection and combination of suitable substituents within the scope of the invention to provide absorption dyes and fluorescent dyes in which, depending on the application purpose, the hydrophilic or lipophilic properties predominate and which can be used in broad wavelength ranges above 600 nm. Moreover the new compounds according to the present invention also have a greatly improved quantum yield which leads to a substantial increase in sensitivity.

When used in hapten/antibody/protein conjugates it is advantageous when the dyes are readily water-soluble. Therefore for this purpose compounds of the general formula (Ia) or (Ib) are preferably used in which $R^1$ and $R^{13}$ are as hydrophilic as possible. These compounds are preferably asymmetrically substituted products which for example contain carboxyl as well as sulfonic acid groups and in which the residues $R^1$ and $R^{13}$ are different. Coupling to the conjugate is preferably carried out via the residues $R^1$, $R^7$ or/and $R^{13}$ and in particular via a N-hydroxysuccinimide group.

Conjugates of the fluorescent dyes with haptens such as e.g. theophylline, digoxin, T3, T4 or proteins such as e.g. antibodies, are for example suitable for use in diagnostic systems in particular for fluorescent immunoassays.

A further type of application for the new compounds is their use in dyeing latices. The latices are preferably dyed by adsorptively integrating suitable dyes into these particles and this requires that the compounds acting as dyes are sufficiently lipophilic. An adequate lipophilicity is achieved for this in particular by selection of a suitable substituent $R^7$ which should be as lipophilic as possible. Thus for example the lipophilic character of the compounds of formula (Ia) or (Ib) can be increased by incorporating longer lipophilic residues in the meaning of $R^7$ e.g. by replacing trifluoromethyl by the longer heptafluoropropyl residue or by use of longer and branched alkyl residues and also of aryl substituents. Compounds of formula (Ia) and (Ib) with a rhodamine structure that contain a 3,4,5,6-tetrahalo-2-carboxyphenyl substituent as residue $R^7$, in which halo is preferably chlorine, are also particularly suitable. Latex particles dyed accordingly can be coated with proteins using the usual methods and used in diagnostic systems.

Typical examples of water-soluble dyes according to the present invention for use in hapten/antibody/protein conjugates are for example the aforementioned compounds (7), (9) and in particular (11). Examples of compounds according to the present invention which are very well suited for incorporation into latices are for example the aforementioned compounds (1), (3), (4), (5), (12) and (18).

The excitation wavelength can be optimized and finely matched to the light sources intended for the application by suitable selection and combination of the substituents.

The invention therefore also concerns the use of compounds according to the present invention as absorption or fluorescent dyes, as an excitation and emission medium in a dye laser and in particular their use in diagnostic systems; and their use for hapten/antibody/protein conjugates in particular in diagnostic systems.

When used as markers for hapten/antibody/protein conjugates, in particular in diagnostic systems, a compound of formula (Ia) and/or (Ib) is preferably employed in which the residues $R^1$ and $R^{13}$ are chosen so that they are as hydrophilic as possible; coupling to the conjugate is preferably carried out via residues $R^1$, $R^7$ and/or $R^{13}$ and preferably by means of a N-hydroxysuccinimide group.

A further use for the compounds according to the present invention is to dye latices whereby compounds of formula (Ia) and/or (Ib) are preferably used in which residue $R^7$ is as lipophilic as possible. Since such latices are very well suited for application in diagnostics the invention also concerns the use of such latices in diagnostics.

A further subject matter is also the use of compounds according to the present invention as an absorption medium for solar collectors.

The present invention furthermore concerns a method according to claim 18 for the determination of a first immunologically bindable substance which is characterized in that a conjugate of a compound according to the present invention with a second immunologically bindable substance which can be the same as or different from the first substance is used and the absorption or change in fluorescence of the compound according to the present invention caused by an immunological binding reaction which is specific for the first substance is determined as a measure for the amount of substance to be determined present in the sample.

DETAILED DESCRIPTION OF THE INVENTION

The following examples are intended to elucidate the present invention in more detail without limiting it thereto.

EXAMPLE 1

7-methoxy-2,2,4-trimethyl-1,2,3,4-tetrahydroquinoline 30 g (0.147 mol) 7-methoxy-2,2,4-trimethyl-1,2-dihyroquinoline (produced according to A. Rosowsky and E. J. Modest, J. Org. Chem. 30 (1965) 1832) is dissolved in 100 ml methanol and admixed with 2.5 g palladium on active charcoal (10%). The substance is hydrogenated for 12 hours at room temperature and at a pressure of 70 bar hydrogen. After the reaction is completed the catalyst is removed by filtration and the solvent is removed in a rotary evaporator. The product crystallizes in the form of a wax-like, light-green product. Yield: 95%.

Thin layer chromatography: silica gel/chloroform+2% ethanol

| - NMR - data: in CDCl$_3$ | | |
|---|---|---|
| $\delta = 1.2$ ppm | 2-CH$_3$ | singlet |
| $\delta = 1.5$ ppm | —CH$_3$ + —CH$_2$— | multiplet |
| $\delta = 2.8$ ppm | —C$^4$—H | multiplet |
| $\delta = 3.6$ ppm | —NH— | singlet |
| $\delta = 3.7$ ppm | —OCH$_3$ | singlet |
| $\delta = 6.1$ ppm | C$^8$—H | doublet |
| $\delta = 6.3$ ppm | C$^6$—H | quartet |
| $\delta = 7.1$ ppm | C$^5$—H | doublet |
| $\delta = 7.24$ ppm | CHCl$_3$ | |

EXAMPLE 2

N-ethyl-7-methoxy-2,2,4-trimethyl-1,2-dihydroquinoline 10 g (0.049 mol) 7-methoxy-2,2,4-trimethyl-1,2-dihydroquinoline (produced according to A. Rosowsky and E. J. Modest, l.c.) is dissolved in 100 ml anhydrous acetonitrile and boiled under reflux for 18 hours with 13.1 g (0.1 mol) anhydrous potassium carbonate and 9.3 g (0.06 mol) ethyl iodide. The cooled reaction mixture is subsequently filtered and the solvent is distilled off. The crude product is a light-green coloured oil. Yield: 80%.

Thin layer chromatography: silica gel/methylene chloride

| - NMR - data: in CDCl$_3$ | | |
|---|---|---|
| $\delta = 1.3$ ppm | 2-CH$_3$ + —CH$_3$ (ethyl group) | multiplet |
| $\delta = 1.95$ ppm | vinyl —CH$_3$ | singlet |
| $\delta = 3.7$ ppm | —OCH$_3$ | singlet |
| $\delta = 4.3$ ppm | —CH$_2$— (ethyl group) | quartet |
| $\delta = 5.15$ ppm | vinyl —H | singlet |
| $\delta = 6.2$ ppm | C$^8$—H + C$^6$—H | multiplet |
| $\delta = 6.95$ ppm | C$^5$—H | doublet |
| $\delta = 7.24$ ppm | CHCl$_3$ | |

EXAMPLE 3

N-ethyl-7-hydroxy-2,2,4-trimethyl-1,2-dihydroquinoline 20 g (0.086 mol) of N-ethyl-7-methoxy-2,2,4-trimethyl-1,2-dihydroquinoline produced according to example 2 is heated to boiling point with 50 ml glacial acetic acid 50 ml hydrobromic acid (45%) for 6 hours. 200 ml water and 300 ml chloroform are added to the cooled reaction mixture. Subsequently the reaction mixture is neutralised with 30 % aqueous sodium hydroxide while cooling. The phases are separated and the aqueous phase is further extracted twice with 100 ml chloroform each time. The organic phases are pooled and dried over calcium chloride. After complete removal of the solvent in a rotary evaporator a light-green oil remains. Yield: 85%.

EXAMPLE 4

N-ethyl-7-methoxy-2,2,4-trimethyl-1,2,3,4-tetrahydroquinoline

The 7-methoxy-2,2,4-trimethyl-1,2,3,4-tetrahydroquinoline obtained according to example 1 is converted into the N-ethyl derivative analogous to the alkylation method described in example 2. Yield: 90%.

EXAMPLE 5

N-ethyl-7-hydroxy-2,2,4-trimethyl-1,2,3,4-tetrahydroquinoline

The N-ethyl-7-methoxy-2,2,4-trimethyl-1,2,3,4-tetrahydroquinoline obtained according to example 4 is converted into the 7-hydroxy compound as described in example 3.

EXAMPLE 6

Production of compound (3)

4 g (0.018 mol) N-ethyl-7-hydroxy-2,2,4-trimethyl-1,2-dihyroquinoline, 4.3 g (0.015 mol) tetrachlorophthalic acid anhydride and 2.5 g (0.018 mol) zinc chloride are mixed thoroughly together and heated to 170° C. for 5 h in an oil bath. The cooled melt is pulverized, boiled out with 500 ml ethanol and filtered. The filtrate is firstly admixed with 100 ml 60% perchloric acid and subsequently dropwise with 400 ml water. The precipitated dye is filtered off and dried.
Column chromatography Silica gel/chloroform+4% ethanol The pooled dye fractions are evaporated to dryness, taken up in 200 ml ethanol, filtered and 50 ml 60% perchloric acid is added dropwise. Subsequently ca. 600 ml water is added dropwise. The filtered dye is washed with ether and dried.

| - NMR - data: in DMSO-$d_6$ | | |
|---|---|---|
| $\delta$ = 1.3 ppm | —CH$_3$ (ethyl group) | triplet |
| $\delta$ = 1.5 ppm | — CH$_3$ | doublet |
| $\delta$ = 1.85 ppm | vinyl-CH$_3$ | singlet |
| $\delta$ = 2.5 ppm | DMSO | |
| $\delta$ = 3.75 ppm | —CH$_2$— (ethyl group) | quartet |
| $\delta$ = 5.75 ppm | vinyl-H | singlet |
| $\delta$ = 6.7 ppm | aromatic H | singlet |
| $\delta$ = 6.9 ppm | aromatic H | singlet |

EXAMPLE 7

Production of compound (4)

4 g (0.018 mol) of the N-ethyl-7-hydroxy-2,2,4-trimethyl-1,2,3,4-tetrahydroquinoline obtained according to example 5, 4.3 g (0.015 mol) tetrachlorophthalic acid anhydride and 2.5 g (0.018 mol) zinc chloride are mixed thoroughly together and heated to 170° C. for 5 h in an oil bath. The cooled melt is pulverized, boiled out with 500 ml ethanol and filtered. The filtrate is firstly admixed with 100 ml 60% perchloric acid and subsequently dropwise with 400 ml water. The precipitated dye is filtered off and purified by means of column chromatography (Alox N/ethanol).

EXAMPLE 8

Production of compound (6)

1 g (5.2 mmol) N-ethyl-7-methoxy-1,2,3,4-tetrahydroquinoline is dissolved in 15 ml anhydrous methylene chloride and admixed with 0.5 ml trifluoroacetic acid and 3.2 g (15 mmol) trifluoroacetic acid anhydride in an ice bath under protection by nitrogen. The reaction mixture is subsequently stirred for 72 h at room temperature while excluding air. Afterwards the methylene chloride and excess trifluoroacetic acid anhydride are removed by distillation. 20 ml 70% sulphuric acid is added to the oily residue and heated to 130° C. for 30 min in an oil bath. 300 ml ethanol and 50 ml 60% perchloric acid are added to the cooled red solution while cooling. 250 ml water is slowly added dropwise to this. The precipitated dye is filtered off, washed with ether and dried.

Chromatography: silica gel/chloroform+10% ethanol

| NMR - data: in $d_6$-DMSO | | |
|---|---|---|
| $\delta$ = 1.2 ppm | —CH$_3$ (ethyl group) | triplet |
| $\delta$ = 1.95 ppm | —C$^3$, $^9$H$_2$ | quintet |
| $\delta$ = 2.5 ppm | DMSO | |
| $\delta$ = 2.85 ppm | —C$^4$, $^3$H$_2$— | triplet |
| $\delta$ = 3.7 ppm | —C$^2$, $^{10}$H$_2$— + —CH$_2$— (ethyl group) | |
| $\delta$ = 6.95 ppm | aromatic H (—C$^{12,14}$—H) | singlet |
| $\delta$ = 7.65 ppm | aromatic H (—C$^{5,7}$—H) | singlet |

EXAMPLE 9

Production of compound (15)

Compound 15 is synthesized analogous to the method set forth in example 8 using the appropriate starting products (N-ethyl-7-methoxy-2,2,4-trimethyl-1,2-dihydroquinoline according to example 2; trifluoroacetic acid anhydride). In order to produce the dye, the oily residue is heated to 140° C. for 1 hour in 70% sulphuric acid. The purification is carried analogous to example 8.

EXAMPLE 10

Production of compound (16)

1.62 g (5 mmol) 3-(7-methoxy-2,2,4-trimethyl-1,2-dihydroquinol-1-yl)-propanesulfonic acid is suspended in 50 ml anhydrous methylene chloride and 4 ml (5.95 g=0.028 mol) trifluoroacetic acid anhydride is added. The solution which turns dark-green is stirred for 12 hours at room temperature while excluding air; subsequently it is filtered and the solvent is removed completely by distillation. 20 ml 70% sulphuric acid is added to the residue and heated to 130° C. for 1 hour. Potassium hydrogen carbonate is added to the red cooled solution until a pH of 4 to 5 is reached. The paste is dried and subsequently suspended in a solution of chloroform containing 10% methanol. The filtered dye solution is purified chromatographically (silica gel/chloroform (250 ml)+ethanol (250 ml)+perchloric acid (60%; 0.5 ml)).

3-(7-methoxy-2,2,4-trimethyl-1,2-dihydroquinol-1-yl-propanesulfonic acid is produced as follows 10.16 g (0.05 mol) 7-methoxy-2,2,4-trimethyl-1,2-dihydroquinoline is heated to 150° C. for 2 hours with 6.7 g (0.055 mol) propanesulfone under nitrogen protection. The cooled, solidified melt is dissolved in 50 ml 10% aqueous sodium carbonate solution and filtered. The solution is subsequently acidified with 20% hydrochloric acid. The precipitate which comes down is filtered off, washed with acetone and dried.

Yield: 80% colourless solid

Thin layer chromatography: silica gel/chloroform+30% methanol

EXAMPLE 11

Production of compound (11)

1.49 g (4.4 mmol) 4-(7-methoxy-2,2,4-trimethyl-1,2-dihydroquinol-1-yl)-butanesulfonic acid and 0.99 g (4 mmol) 4-(7-methoxy-1,2,3,4-tetrahydroquinol-1-yl)-butyric acid are suspended in 50 ml methylene chloride and admixed with 4 g (0.019 mol) trifluoroacetic acid anhydride. The solution is stirred for 12 hours while excluding air, subsequently filtered and rotary evaporated to dryness. 25 ml 70% sulphuric acid is added to the residue and heated for 30 min to 130° C. Potassium hydrogen carbonate is added to the red solution until a pH value of 4–5 is achieved. The viscous paste is suspended several times in a solution of chloroform containing 20% methanol. The solution is filtered and evaporated to dryness. The residue is purified chromatographically (silica gel). Dye (7) is firstly separated using a mixture of chloroform containing 15% ethanol and 0.1% perchloric acid (60%). Subsequently the polarity of the mobile solvent is increased by addition of 20% ethanol and dye (11) is obtained.

EXAMPLE 12

Production of compound (21)

0.5 g (2.6 mmol) N-ethyl-7-hydroxy-2,2,4-trimethyl-1,2-dihydroquinoline, 0.3 g (3 mmol) succinic acid anhydride and 0.4 g (3 mmol) zinc chloride are heated for 2 hours to 180° C. The cooled melt is dissolved in ethanol, filtered and 10 ml 60% perchloric acid is added. 1 l water is slowly added dropwise to this. The precipitate is filtered off and dried.

Thin layer chromatography: silica gel/chloroform (85 ml)+ ethanol (15 ml)+perchloric acid (1 ml) (60%)

Column chromatography: silica gel/chloroform+5% ethanol

NMR data: in $d_6$-DMSO

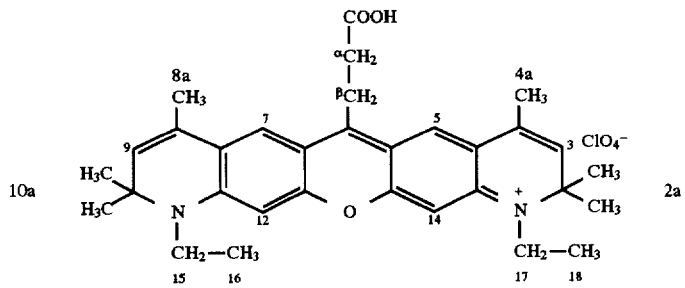

| Chemical shift δ in ppm | Signal form | Integration | Classification |
| --- | --- | --- | --- |
| 1.1 | T | 6H | H-16, H-18 |
| 1.5 | S | 12H | H-2a, H-10a |
| 2.1 | S | 6H | H-4a, H-8a |
| 2.54 | — | — | DMSO |
| 2.75 | T | 2H | H-α |
| 3.7 | M | 6H | H-β, H-15, H-17 |
| 5.77 | S | 2H | H-3, H-9 |
| 6.75 | S | 2H | H-12, H-14 |
| 7.58 | S | 2H | H-5, H-7 |

EXAMPLE 13

Production of compound (22)

2 g (9.6 mmol) N-(2-hydroxyethyl)-7-methoxy-1,2,3,4-tetrahydroquinoline is dissolved in 15 ml methylene chloride and admixed with 10 g (0.048 mol) trifluoroacetic acid anhydride under nitrogen protection. The reaction mixture is stirred for 12 hours at room temperature. Subsequently the methylene chloride and excess trifluoroacetic acid anhydride is removed by distillation. 20 ml 70% sulphuric acid is added to the oily residue and heated to 130° C. for 30 min in an oil bath. After the condensation 100 g ice and 30 ml 60% perchloric acid are added to the cooled sulphuric acid solution. The solution is left to stand for ca. 12 h in the cold and is subsequently filtered. Afterwards the mother liquor is extracted with chloroform until the aqueous phase remains only faintly blue coloured. The pooled organic phases are dried over $Na_2SO_4$ and concentrated by evaporation. The remaining concentrated dye solution is purified chromatographically.

Thin layer chromatography: silica gel/chloroform+5% ethanol

Column chromatography: silica gel/chloroform+5% ethanol+1% trifluoroacetic acid

NMR data: in $CDCl_3$

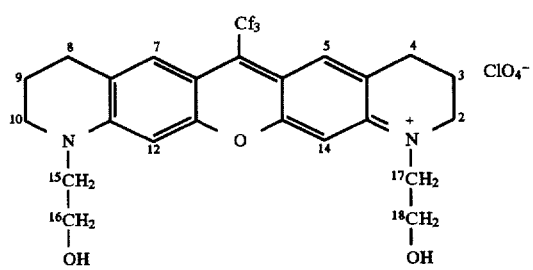

| Chemical shift δ in ppm | Signal form | Integration | Classification |
| --- | --- | --- | --- |
| 2.0 | T | 4H | H-3, H-9 |
| 2.85 | T | 4H | H-4, H-8 |

-continued

— NMR — data: in CDCl₃

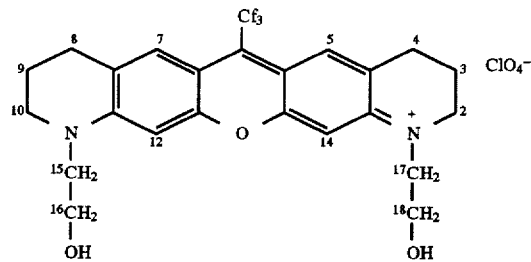

| Chemical shift δ in ppm | Signal form | Integration | Classification |
|---|---|---|---|
| 3.7 | M | 8H | H-2, H-10 H-15, H-17 |
| 3.95 | T | 4H | H-16, H-18 |
| 6.9 | S | 2H | H-12, H-14 |
| 7.55 | S | 2H | H-5, H-7 |

EXAMPLE 14

Production of compound (23)

1.82 g (0.011 mol) 7-methoxy-1,2,3,4-tetrahydroquinoline is stirred with 2.04 g (0.011 mol) 1-bromo-2-(2-methoxyethoxy-)ethane and 1.42 g (0.11 mol) Hünig base for 12 hours at 120° C. After cooling the solution is filtered, the filtered salt is washed with a small amount of acetone and the mother liquor is evaporated to dryness. 20 ml methylene chloride and 0.5 ml trifluoroacetic acid are added to the residue. Subsequently the solution is cooled in an ice/NaCl bath and 5 g trifluoroacetic acid anhydride is added dropwise. The solution is stirred for 12 hours, subsequently evaporated to dryness and 20 ml 70% sulphuric acid is added. Afterwards the solution is heated for 30 min to 130° C. The processing of the cooled solution is carried out analogous to dye JA 49.

Chromatography (educt): silica gel/methylene chloride+5% ethanol

EXAMPLE 15

Production of compound (24)

Preparation: analogous to dye 23 using 2-2[2-chloro-ethoxy)-ethoxy]-ethanol

Chromatography (educt): silica gel/chloroform+5% ethanol+0.2% trifluoroacetic acid

EXAMPLE 16

Production of H-hydroxysuccinimide esters 100 mg of an appropriate carboxylic acid derivative (preferably an acid chloride) is reacted with dicyclohexyl-carbodiimide and N-hydroxysuccinimide under the usual conditions for the production of N-hydroxy-succinimide esters (solvent: tetrahydrofuran or dimethylformamide; room temperature; 4 hours). After removal of the solvent, it is purified by flash chromatography.

EXAMPLE 17

Coupling of activated dyes according to the present invention to proteins (e.g. of a dye produced according to example 11)

10 mg protein is dissolved in 1 ml NaHCO₃ buffer, 0.1 mol/l, pH =8.5. A solution of the dye in DMSO is added to this (one uses an excess corresponding to the desired number of coupled dye molecules). The reaction solution is shaken for 1 hour at room temperature. The conjugate is separated from free dye over a G 50 Sephadex column (mobile solvent: NaHCO₃ buffer), dialysed sufficiently against H₂O and lyophilised.

EXAMPLE 18

Coating latex particles with lipophilic dyes according to the present invention 5 ml 1% latex suspension (e.g. polystyrol latices from the Polyscience Company) is admixed with 1 mg of the dye according to the present invention dissolved in 200 μl chloroform and shaken for ca. 20 hours. The solvent is removed by passing in nitrogen and the free dye particles are separated by centrifugation or filtration.

EXAMPLE 19

Determination of the fluorescence quantum yield of compound (15)

Solutions of the dye according to the present invention and of rhodamine 800 (cf. R. Raue, H. Harnisch, K. H. Drexhage, Heterocycles 21(1), 167, (1984)) (reference substance) in ethanol are prepared and the concentration is adjusted so that the absorbance of each solution is 1.7/mm at a wavelength of 676 nm. The fluorescence spectra of the solutions are then measured in a 1 mm cuvette (front surface measurement) using a Fluorolog 2 spectrofluorimeter from the Spec Company (excitation wavelength 676 nm) using the same instrument parameters and the areas under the fluorescence curves are determined. By comparison with the reference dye rhodamine 80, whose quantum yield is 21% (cf. R. Sens, Dissertation, Siegen 1984) this results in a quantum yield of e.g. 55% for compound (15) according to the present invention.

EXAMPLE 20

Production of compound (25)

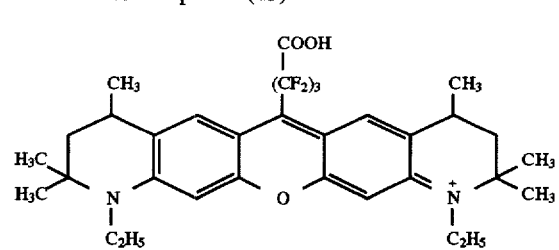

0.5 g (2.1 mmol) N-ethyl-7-methoxy-2,2,4-trimethyl-1,2,3,4-tetrahydroquinoline is dissolved in 15 ml methylene chloride and admixed with 2 drops trifluoroacetic acid and 1.5 g (6.8 mmol) perfluoroglutaric acid anhydride. The solution which turns an intensive green is stirred for 5 hours at room temperature. The solution is evaporated to dryness on a rotary evaporator and the supernatant is heated to ca. 130° C. in 20 ml 70% sulphuric acid for 30 min. The cooled red solution is fed into ca. 100 ml ethanol while cooling. 10 ml perchloric acid (60%) and subsequently ca. 200 ml water are slowly added dropwise to this. The precipitate is filtered off, washed with ether and dried (yield 0.5 g=67%).

Absorption maximum in ethanol: 634 nm

¹H-NMR data: in d₆ acetone

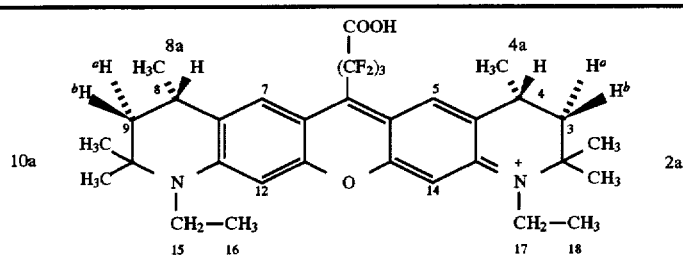

| Chemical shift δ in ppm | Signal form | Integration | Classification |
|---|---|---|---|
| 1.45 | M | 24H | H-2a, H-4a, H-8a, H-10a, H-16 H-18 |
| 1.7 | T | 2H | H-3a, H-9a |
| 2.05 | — | — | acetone |
| 2.1 | DvD | 2H | H-3b, H-9b |
| 3.1 | QI | 2H | H-4, H-8 |
| 3.87 | M | 4H | H-15, H-17 |
| 6.95 | S | 2H | H-12, H-14 |
| 7.75 | S | 2H | H-5, H-7 |

EXAMPLE 21

Production of compound (26)

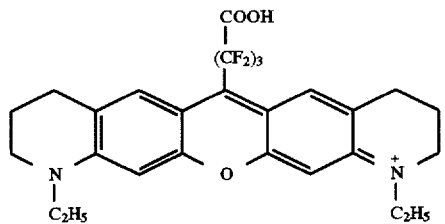

Preparation: analogous to Example 20 using N-ethyl-7-methoxy-1,2,3,4-tetrahydroquinoline as the starting material.

Absorption maximum in ethanol: 630 nm.

We claim:

1. A compound of the formula

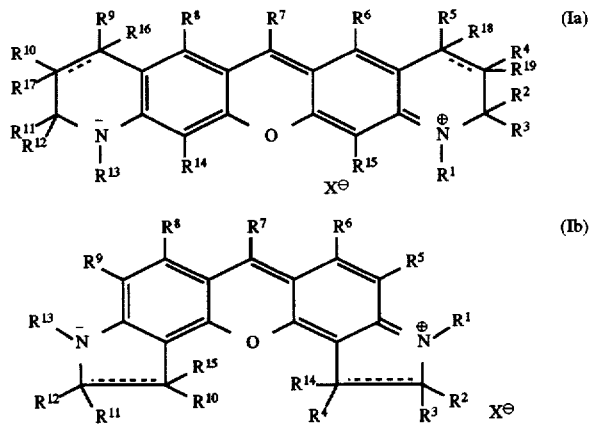

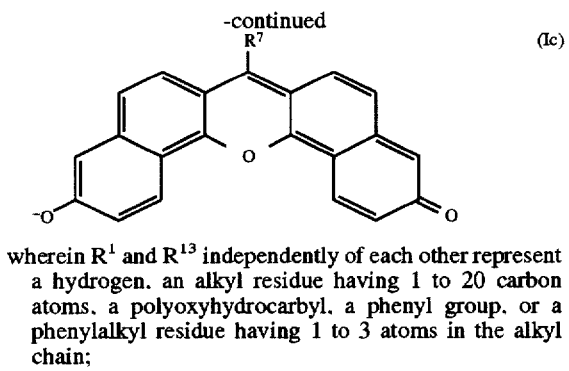

wherein $R^1$ and $R^{13}$ independently of each other represent a hydrogen, an alkyl residue having 1 to 20 carbon atoms, a polyoxyhydrocarbyl, a phenyl group, or a phenylalkyl residue having 1 to 3 atoms in the alkyl chain;

$R^7$ is (i) an alkyl group of 1 to 20 carbon atoms, substituted by at least one halogen, (ii) a phenyl group, substituted by a carboxy or an alkoxycarbonyl group having 1 to 4 carbon atoms, wherein said carboxy or alkoxycarbonyl group is located in the ortho position of the carbon atom bound to a pentacyclic ring system of said compound and by at least one halogen, (iii) a carboxy group, (iv) a carboxyalkyl group having 1 to 10 carbon atoms in the alkylene chain, or (v) a carboxymethylene-oxy-alkyloxy group;

$X^{\ominus}$ is a counterion;

$R^2$, $R^3$, $R^4$, $R^5$, $R^6$, $R^8$, $R^9$, $R^{10}$, $R^{11}$, $R^{12}$, $R^{14}$, $R^{15}R^{16}$, $R^{17}$, $R^{18}$, and $R^{19}$ independently of each other represent a hydrogen, an alkyl or a substituted alkyl having 1 to 20 carbons and two of $R^2$, $R^3$, $R^4$, $R^5$, $R^6$, $R^8$, $R^9$, $R^{10}$, $R^{11}$, $R^{12}$, $R^{14}$, $R^{15}$, $R^{16}$, $R^{17}$, $R^{18}$, and $R^{19}$ are optionally linked together;

---- represents a single or double bond; wherein said compound can be activated at at least one of $R^1$, $R^7$ and $R^{13}$.

2. A compound of claim 1, wherein at least one of $R^1$ or $R^{13}$, is an alkyl or phenyl group substituted by a hydroxy, a halogen, a sulfo group, a carboxy group or an alkoxycarbonyl group having 1 to 4 carbon atoms.

3. A compound of claim 1, wherein at least one of $R^2$, $R^3$, $R^4$, $R^5$, $R^6$, $R^8$, $R^9$, $R^{10}$, $R^{11}$, $R^{12}$, $R^{14}$, $R^{15}$, $R^{16}$, $R^{17}$, $R^{18}$, and $R^{19}$ is a substituted alkyl.

21

4. A compound of claim 1, wherein at least two of $R^2$, $R^3$, $R^4$, $R^5$, $R^6$, $R^8$, $R^9$, $R^{10}$, $R^{11}$, $R^{12}$, $R^{14}$, $R^{15}$, $R^{16}$, $R^{17}$, $R^{18}$, and $R^{19}$, are linked together.

5. A compound of claim 1, wherein at least one of $R^1$ and $R^{13}$, is a hydrogen, an optionally substituted group of 1 to 4 carbon atoms, or a benzyl group.

6. A compound of claim 5, wherein said alkyl is substituted by a hydroxy, a halogen, a carboxy group, an alkoxycarbonyl group, or a sulfo group.

7. A compound of claim 1, wherein at least one of $R^1$ and $R^{13}$ is a polyoxyhydrocarbyl.

8. A compound of claim 7, wherein said polyoxyhydrocarbyl is a polyether, a polyol, a water soluble carbohydrate, or a water soluble carbohydrate substituted by amino or acid groups.

9. A compound of claim 1, wherein $R^7$ is a perhalogenated alkyl group having 1 to 3 carbon atoms.

10. A compound of claim 9, wherein $R^7$ is a perfluorinated alkyl group having 1 to 3 carbon atoms.

11. A compound of claim 1, wherein $R^7$ is a carboxyalkyl group having 1–10 carbon atoms in the alkylene chain, a carboxy group or a carboxymethylene-oxy-alkyloxy group.

12. A compound of claim 1, having the formula,

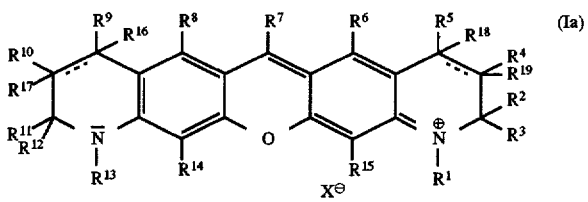

wherein $R^1$ is not linked with $R^{15}$, and $R^{13}$ is not linked with $R^{14}$.

13. A compound of claim 1, wherein at least one of said --- is a double bond.

14. A compound of claim 1, wherein $X^\ominus$ is a perchlorate, a heptafluorobutyrate, COO— or $SO_3$.

15. A compound of claim 1, wherein $R^7$ is an alkyl group having 1 to 7 carbon atoms.

16. A compound of claim 1, wherein $R^1$ and $R^{13}$, independently of each other, represent a hydrogen, a methyl, a ethyl, a 3-sulfopropyl, a 4-sulfobutyl, a 3-carboxypropyl, a 4-carboxybutyl, a 3-methoxycarbonylpropyl, a 3-ethoxycarbonylpropyl, a methoxy-ethoxy-ethyl, a hydroxyethoxy-ethyl, or a benzyl group.

17. A compound of claim 1, wherein $R^7$ is selected from the group consisting of trifluoromethyl, pentafluoroethyl, heptafluoropropyl, a 3,4,5,6-halo-2-carboxyphenyl, a 3,4,5,6-halo-2-ethoxy-carboxyl-phenyl and a carboxyethyl group.

18. A compound of the formula:

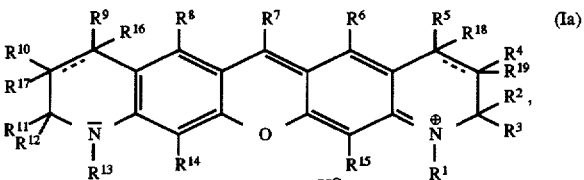

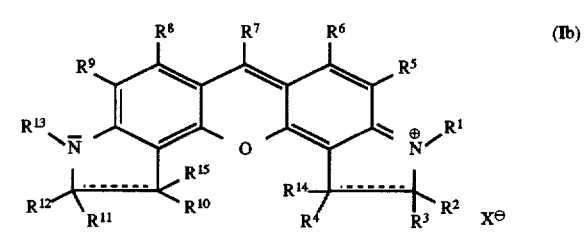

22

-continued and

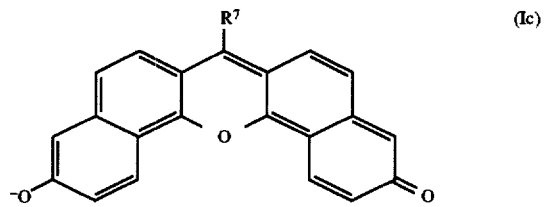

wherein $R^1$ and $R^{13}$ independently of each other represent a hydrogen, an alkyl residue having 1 to 20 carbon atoms, a polyoxyhydrocarbyl, a phenyl residue, or a phenylalkyl residue having 1 to 3 atoms in the alkyl chain;

$R^7$ is (i) an alkyl group of 1 to 20 carbon atoms, substituted by at least one halogen, (ii) a phenyl group, substituted by a carboxy or an alkoxycarbonyl group having 1 to 4 carbon atoms, wherein said carboxy or alkoxycarbonyl group is located in the ortho position of the carbon atom bound to a pentacyclic ring system of said compound and by at least one halogen;

(iii) a carboxy group;

(iv) a carboxyalkyl group having 1 to 10 carbon atoms in the alkylene chain; or (v) a carboxymethylene-oxy-alkyloxy group;

$X^\ominus$ is a counterion;

$R^2$, $R^3$, $R^4$, $R^5$, $R^6$, $R^8$, $R^9$, $R^{10}$, $R^{11}$, $R^{12}$, $R^{14}$, $R^{15}$, $R^{16}$, $R^{17}$, $R^{18}$, and $R^{19}$ independently of each other represent a hydrogen, an alkyl or a substituted alkyl having 1 to 20 carbons and two of $R^2$, $R^3$, $R^4$, $R^5$, $R^6$, $R^8$, $R^9$, $R^{10}$, $R^{11}$, $R^{12}$, $R^{14}$, $R^{15}$, $R^{16}$, $R^{17}$, $R^{18}$, and $R^{19}$ are optionally linked together;

--- represents a single or double bond; wherein said compound can be activated at at least one of $R^1$, $R^7$ and $R^{13}$; and wherein there is an N-hydroxy-succinimide ester or an organic acid chloride at at least one of $R^1$, $R^7$, and $R^{13}$.

19. A method for determining a first immunologically bindable substance in a sample, comprising:

contacting a conjugate of a compound of claim 1 and a second immunologically bindable substance which is bindable with said first immunologically bindable substance, with said sample containing said first immunologically bindable substance, and determining the change in absorption or fluorescence of the compound caused by immunological binding which is specific for the first immunologically bindable substance as a measure of the amount of said first immunologically bindable substance in said sample.

20. A method for determining a first immunologically bindable substance in a sample, comprising:

contacting a conjugate of the compound of claim 1 and a second immunologically bindable substance, with a known amount of a binding partner which binds to said first immunologically bindable substance and to said second immunologically bindable substance, and with said sample containing said first immunologically bindable substance, and determining the change in absorption or fluorescence of the compound caused by immunological binding which is specific for the first immunologically bindable substance in said sample as a measure of the amount of said first immunologically bindable substance.

* * * * *

UNITED STATES PATENT AND TRADEMARK OFFICE
CERTIFICATE OF CORRECTION

PATENT NO. : 5,750,409
DATED : May 12, 1998
INVENTOR(S) : Herrmann et al.

It is certified that error appears in the above-identified patent and that said Letters Patent is hereby corrected as shown below:

In column 2, lines 30-31, change "opposition" to -- o-position --.

In column 4, line 4, after "meaning" delete -- ; -- ; after "defined" insert -- ; --.

In column 7, last line, change "570 nm" to -- 670 nm --.

In column 8, line 9, change "542 nm" to -- 642 nm --.

In column 8, line 45, change "(CH$_2$)$_3$" to -- (CH$_2$)$_2$ --.

In column 9, line 27, delete "R".

In column 9, line 28, change "ömpps' " to -- Römpps' --.

In column 11, line 64, change " -1,2.3.4- " to -- -1,2,3,4- --.

In column 11, line 67, change "dihyroquiniline" to --dihydroquinoline--.

In column 13, line 16, change "dihyroquiniline" to --dihydroquinoline--.

In column 20, line 52, between "R$^{15}$" and "R$^{16}$" add -- , --.

Signed and Sealed this

Fifth Day of September, 2000

Attest:

Q. TODD DICKINSON

*Attesting Officer*    *Director of Patents and Trademarks*